United States Patent
Isozaki et al.

(10) Patent No.: US 8,009,286 B2
(45) Date of Patent: Aug. 30, 2011

(54) SURFACE INSPECTING METHOD AND DEVICE

(75) Inventors: Hisashi Isozaki, Tokyo (JP); Takehiro Takase, Tokyo (JP); Takashi Kakinuma, Tokyo (JP); Hiroyuki Maekawa, Tokyo (JP); Fumio Koda, Tokyo (JP); Michihiro Yamazaki, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 346 days.

(21) Appl. No.: 12/442,879

(22) PCT Filed: Dec. 4, 2007

(86) PCT No.: PCT/JP2007/073744
§ 371 (c)(1),
(2), (4) Date: Mar. 25, 2009

(87) PCT Pub. No.: WO2008/108041
PCT Pub. Date: Sep. 12, 2008

(65) Prior Publication Data
US 2010/0007872 A1    Jan. 14, 2010

(30) Foreign Application Priority Data
Mar. 6, 2007 (JP) .................. 2007-055663

(51) Int. Cl.
*G01N 21/00* (2006.01)
(52) U.S. Cl. .................. 356/237.3; 356/237.1
(58) Field of Classification Search ........... 356/237.1, 356/237.2–237.5, 337, 338, 341, 343
See application file for complete search history.

(56) References Cited

U.S. PATENT DOCUMENTS

| 5,995,217 | A | * | 11/1999 | Watanabe ................. 356/237.1 |
| 6,157,444 | A | * | 12/2000 | Tomita et al. ............. 356/237.1 |
| 7,465,935 | B2 | | 12/2008 | Urano et al. |
| 7,502,102 | B2 | * | 3/2009 | Johannesson et al. ..... 356/237.2 |
| 2005/0200850 | A1 | * | 9/2005 | Borden et al. ............. 356/432 |

(Continued)

FOREIGN PATENT DOCUMENTS
JP    1-221850 A    9/1989
(Continued)

OTHER PUBLICATIONS

K. Takeda, "Simultaneous Measurement of Size and Depth of Each Defect in a Silicon Wafer Using Light Scattering at Two Wavelengths" OSDA, vol. 22, No. 5, pp. 323-331, 2001.

*Primary Examiner* — Tarifur Chowdhury
*Assistant Examiner* — Michael LaPage
(74) *Attorney, Agent, or Firm* — Foley & Lardner LLP

(57) ABSTRACT

A light source section outputs optical flux having two types of wavelength, which are a short wavelength and a long wavelength, while the intensity is made variable. The output from the first light intensity detecting section in irradiating the optical flux having a short wavelength is compared with the output from the first light intensity detecting section in irradiating the optical flux having a long wavelength. A disappearance level near a point where the detected signal from the internal subject disappears is calculated. The first intensity of optical flux having a long wavelength is set to level higher than the disappearance level. Based on the output from the first light intensity detecting section obtained by the optical flux having a long wavelength of the first intensity, a subject inside the body to be detected is measured.

14 Claims, 3 Drawing Sheets

U.S. PATENT DOCUMENTS

2006/0244958 A1 * 11/2006 Furman et al. ............. 356/237.4

FOREIGN PATENT DOCUMENTS

| | | | |
|---|---|---|---|
| JP | 6-331559 | A | 12/1994 |
| JP | 6-331567 | A | 12/1994 |
| JP | 7-294422 | A | 11/1995 |
| JP | 11-148903 | A | 6/1999 |
| JP | 11-237226 | A | 8/1999 |
| JP | 11-354598 | A | 12/1999 |
| JP | 2001-108639 | A | 4/2001 |
| JP | 2004-279218 | A | 10/2004 |
| JP | 2006-201044 | A | 8/2006 |
| JP | 2006-258582 | A | 9/2006 |
| WO | WO 97/35162 | A1 | 9/1997 |

* cited by examiner

SURFACE INSPECTING METHOD AND DEVICE

BACKGROUND OF THE INVENTION

1. Field of the Invention

The present invention relates to a method and an apparatus for inspecting the surface of a semiconductor wafer or other body to be detected.

2. Related Art

A method and an apparatus in which defects inside a wafer is inspected by using dual-wavelength laser beam are publicly known. See Japanese Patent Unexamined Publications No. 11-354598, No. 11-237226, and Paper "Measuring technology of the size and the depth of surface defects on the entire wafer surface caused by two-wavelength beam scattering (OSDA: Optical Shallow Defect Analyzer)" written by Takeda Kazuo in Journal of Surface Science and Nanotechnology vol. 22, No. 5, pp. 323-331, 2001.

For example, internal measurement and surface measurement of a wafer are made possible by a wavelength difference between two wavelengths (difference between a short wavelength and a long wavelength).

SOI calibration cannot be performed by the surface inspection of a conventional dual-wavelength method. In addition, it has been impossible to quantitatively measure the information of interior interface of an SOI wafer.

Although foreign particle measurement on the surface of a thin film SOI wafer of the next generation can be performed by using a short wavelength (DUV), influence of a wafer base material cannot be quantitatively measured by the surface inspection of the conventional dual-wavelength method. For example, interface between a middle layer and a lower layer cannot be measured accurately. Particularly, small cavities or foreign particles inside a wafer cannot be accurately measured. This has caused an adverse effect in the yield of devices.

SUMMARY OF THE INVENTION

It is an object of the present invention to provide a surface inspection method and an apparatus, which are capable of accurately measuring the inside of a body to be detected (e.g. wafer), having a multilayer structure, by a dual-wavelength method.

It is another object of the present invention to provide a surface inspection method and an apparatus, which are capable of highly precisely measuring the defects or the foreign particles inside the body to be detected, including a thin film SOI or a multilayer structure having characteristics in conformance with the SOI, contribute to improved yield, and capable of improving the quality of material.

According to the present invention which is an improved surface inspection method and apparatus, optical flux having two types of wavelength, which are a short wavelength and a long wavelength, is made incident to the detected surface to be detected of a body to be detected, which is a subject of surface inspection at a predetermined incident angle so as to detect a subject to be detected, that is a foreign particle, for example.

On one hand, optical flux having a short wavelength is made incident to the surface of a body to be detected, so as to measure foreign particles on the surface of the body to be detected.

On the other hand (or after the measurement by short wavelength), the intensity of optical flux having a long wavelength is adjusted to measure foreign particles inside the body to be detected (in this case, the foreign particles includes narrowly-defined foreign particle, defects, cavities, COPs or the like).

For example, in one embodiment of the present invention, the intensity of optical flux having a long wavelength is adjusted, a disappearance level near a point where a detected signal from the internal subject disappears is calculated, the first intensity of the optical flux having a long wavelength is set to a level higher than the disappearance level, and a subject inside the body to be detected is measured based on the output of the first intensity obtained by the optical flux having a long wavelength of the first light intensity.

In another embodiment of the present invention, foreign particles which are measured when the intensity of the optical flux having a long wavelength is set to "Weak or Low" are subtracted from foreign particles which are measured when the intensity of the optical flux having a long wavelength is set to "Strong or High". Further, residual foreign particles are judged as foreign objects including COPs or defects inside the body to be detected.

The body inspected according to the present invention has, for example, a multilayer structure including a surface layer, a middle layer and a lower layer (each layer is usually correspond to the first layer, the second layer, the third layer) from the surface in order, and preferably subjects to be detected such as foreign particles exist mainly on the boundary between each layer in large number.

In another embodiment of the present invention, the first intensity of the optical flux having a long wavelength is set to a level higher than the disappearance level. The subject to be detected that belongs to the lower layer inside body to be detected is measured based on the output of the first intensity obtained by the optical flux having a long wavelength of the first light intensity. The second intensity of the optical flux having a long wavelength is set to a level lower than the disappearance level. Further a subject to be detected that belongs to the middle layer inside the body to be detected is measured based on the output the first light intensity obtained by optical flux having a long wavelength of the second intensity.

Preferably, optical flux in the ultraviolet region is outputted as a short wavelength, and optical flux in the visible region is outputted as a long wavelength. In this case, a preferable example of the body to be detected is a thin film SOI wafer. Layers of Si, SiO and Si are formed from the surface of the thin film SOI wafer in order as a multilayer structure. Further, optical flux in the deep ultraviolet region (DUV: Deep Ultraviolet) can be also outputted as a short wavelength. In this case, the body to be detected is a wafer, and it is preferable that a subject to be detected on the wafer be foreign particles on wafer surface and foreign objects including COPs or defects inside a wafer (particularly, boundary between middle layer and lower layer).

Further, it is preferable to coaxially output optical flux having two types of wavelength: a short wavelength and a long wavelength.

Further, in another preferable embodiment of the present invention, the surface inspection apparatus is equipped with: a light source section that outputs optical flux having two types of wavelength (a short wavelength and a long wavelength) while the intensity of the flux is made variable; an irradiation optical system that allows the optical flux having two types of wavelength outputted from the light source section to be simultaneously or alternatively made incident to the surface of a body to be detected, which is a subject of surface inspection at a predetermined incident angle; a scanning section that relatively displaces at least one of the optical flux and the body to be detected such that the optical flux scans the surface to be detected; a scattering light detection optical system that guides scattering light outputted from the incident portion of the surface to be detected, to which the optical flux has been made incident, to the first light intensity detecting section; a scattering light detection optical system that guides regular reflection light outputted from the incident portion of the detected surface, to which the optical flux has been made incident, to the second light intensity detecting section; and a controlling arithmetic section that adjusts at least the intensity of the optical flux having a long wavelength outputted from the light source section based on a type of optical flux outputted from the light source section and an output from the first light intensity detecting section.

The controlling arithmetic section of the surface inspection apparatus is constituted so as to compare the output from the first light intensity detecting section in irradiating the optical flux having a short wavelength with the output from the first light intensity detecting section in irradiating the optical flux having a long wavelength, identify a signal that appears only in the output from the first light intensity detecting section in irradiating the optical flux having a long wavelength as a detected signal from an internal subject, and adjust the intensity of the optical flux having a long wavelength, calculate a disappearance level near a point where the detected signal from the internal subject disappears, set the first intensity of the optical flux having a long wavelength to a level higher than the disappearance level, measure a subject inside the body to be detected based on the output from the first light intensity detecting section obtained by the optical flux having a long wavelength of the first intensity.

Preferably, the above-described controlling arithmetic section is constituted so as to set the first intensity of the optical flux having a long wavelength to a level higher than the disappearance level, measure a subject to be detected that belongs to the lower layer inside body to be detected based on the output from the first light intensity detecting section obtained by the optical flux having a long wavelength of the first intensity, set the second intensity of the optical flux having a long wavelength to a level lower than the disappearance level, and measure a subject to be detected that belongs to the middle layer inside the body to be detected based on the output from the first light intensity detecting section obtained by the optical flux having a long wavelength of the second intensity.

It is preferable that the above-described light source section outputs the optical flux in the ultraviolet region as a short wavelength and outputs the optical flux in the visible region as a long wavelength.

The above-described light source section can be also constituted to output optical flux in the deep ultraviolet region (DUV: Deep Ultraviolet) as a short wavelength.

Further, it is preferable that the above-described light source section coaxially outputs the optical flux having two types of wavelength, which are a short wavelength and a long wavelength, and make the intensity of the flux variable.

Furthermore, description will be specifically made for a preferable light source section.

It is preferable to use 213 nm, 266 nm and 355 nm, for example, as the wavelength of deep ultraviolet ray. These wavelengths can be form by extracting fifth harmonic, fourth harmonic, third harmonic respectively from a YAG solid-state laser (fundamental wave: 1064 nm) by a non-linear optical crystal such as a CBO crystal (cesium triborate crystal) and a CLBO crystal (cesium lithium borate crystal).

Describing an example of a preferable constitution of visible light beam, a blue semiconductor laser can be used as 408 nm, and an Ar laser solid-state laser can be used as 488 nm.

According to the present invention, the inside and the surface layer of an SOI wafer or another wafer, which has a multilayer film structure, can be measured by two wavelengths. For example, inspection of foreign particles is performed to the inside of a wafer. Particularly, scattered quantity on interface is measured. Thus, interface condition is grasped, and internal foreign particles/defects measurement and measurement of interface of the SOI wafer are made possible. As a result, quality improvement can be achieved. Moreover, SOI calibration can be performed by using foreign objects including COPs or defects inside wafer.

Modes of the present invention are summarized as follows:
(1) A surface inspection apparatus comprising:
a light source section that outputs optical flux having two types of wavelength, which are a short wavelength and a long wavelength, while the intensity of the flux is made variable;
an irradiation optical system that makes the optical flux having two types of wavelength outputted from said light source section, incident simultaneously or alternatively to a detected surface of a body to be detected, which is a subject of surface inspection at a predetermined incident angle;
a scanning section that relatively displaces at least one of said optical flux and said body to be detected in such a manner that said optical flux scans said detected surface;
a first scattering light detection optical system that guides scattering light outputted from the incident portion of said detected surface, to which said optical flux has been made incident, to a first light intensity detecting section;
a second scattering light detection optical system that guides regular reflection light outputted from the incident portion of said detected surface, to which said optical flux has been made incident, to a second light intensity detecting section; and
a controlling arithmetic section that adjusts at least the intensity of the optical flux having a long wavelength outputted from the light source section based on a type of optical flux outputted from the light source section and an output from the first light intensity detecting section,
wherein said controlling arithmetic section is constituted so as to compare the output from said first light intensity detecting section in irradiating the optical flux having a short wavelength, with the output from said first light intensity detecting section in irradiating the optical flux having a long wavelength, and then, identify a signal that appears only in the output from said first light intensity detecting section in irradiating the optical flux having a long wavelength, as a detected signal from an internal subject, and further adjusts the intensity of the optical flux having a long wavelength, and then calculate a disappearance level near a point where the detected signal from the internal subject disappears, further set the first intensity of the optical flux having a long wavelength to a level higher than the disappearance level, and measure a subject inside the body to be detected based on the output from the first light intensity detecting section obtained by the optical flux having a long wavelength of the first intensity.

(2) The above-stated surface inspection apparatus, wherein
the body to be detected has a multilayer structure comprising a surface layer, a middle layer and a lower layer in order from surface, wherein subjects to be detected are mainly positioned on the boundary of each layer, and
the controlling arithmetic section is constituted so as to set the first intensity of the optical flux having a long wavelength to a level higher than the disappearance level;

measure a subject to be detected that belongs to the lower layer inside body to be detected based on the output from the first light intensity detecting section obtained by the optical flux having a long wavelength of the first intensity;

set the second intensity of the optical flux having a long wavelength to a level lower than the disappearance level; and measure a subject to be detected that belongs to the middle layer inside the body to be detected based on the output from the first light intensity detecting section obtained by the optical flux having a long wavelength of the second intensity.

(3) The above-stated surface inspection apparatus, wherein the light source section includes outputting the optical flux in the ultraviolet region as a short wavelength and output the optical flux in the visible region as a long wavelength, and the body to be detected is a thin film SOI wafer, wherein layers of Si, $SiO_2$ and Si are formed as a multilayer structure in order from the surface of the thin film SOI wafer.

(4) The above-stated surface inspection apparatus, wherein the light source section is constituted so as to output optical flux in the deep ultraviolet region (DUV: Deep Ultraviolet) as a short wavelength, and Wherein the body to be detected is a wafer, and a detected subject on the wafer is foreign particles on the wafer surface and foreign objects including COPs or defects inside the wafer.

(5) The above-stated surface inspection apparatus, wherein the light source section is constituted so as to coaxially output the optical flux having two types of wavelength, which are a short wavelength and a long wavelength, and make the intensity of the flux variable.

(6) A surface inspection method in which optical flux having two types of wavelength, which are a short wavelength and a long wavelength, is made incident to a detected surface of a body to be detected, which is a subject of surface inspection at a predetermined incident angle and foreign particles are detected, the method including the steps of:

adjusting the intensity of optical flux having a long wavelength so as to calculate a disappearance level near a point where a detected signal from an internal subject disappears, setting a first intensity of the optical flux having a long wavelength to a level higher than the disappearance level, and measuring a subject inside the body to be detected on the basis of the output of the first light intensity which is obtained by the optical flux having a long wavelength of the first intensity.

(7) A surface inspection method in which optical flux having two types of wavelength, which are a short wavelength and a long wavelength, is made incident to a detected surface of a body to be detected, which is a subject of surface inspection at a predetermined incident angle, and foreign particles are detected, the method including the steps of:

adjusting the intensity of optical flux having a long wavelength, subtracting subjects which are measured when the intensity of optical flux having a long wavelength is set to "Weak or Low", from subjects which are measured when the intensity of optical flux having a long wavelength is set to "Strong or High", and judging residual subjects are judged as foreign objects including COPs or defects inside the body to be detected.

(8) The above-stated surface inspection method, wherein a surface layer, a middle layer and a lower layer are a first layer, a second layer and a third layer, respectively, a light having a short wavelength is irradiated to obtain a first measured result on one hand, the light having a long wavelength of high intensity, which is capable of detecting foreign objects including COPs or defects on the third layer inside, is irradiated to obtain a detected image on the other hand, the intensity is lowered to a level where subjects other than the first measured result disappear to make it a standard level, a second measured result is obtained by performing measurement by the first measurement level higher than the level by a predetermined level, a third measured result is obtained by further performing measurement by the second measured level lower than the standard level by a predetermined level, a subject that appears only in the first measured result is judged as one that exists on the surface of the body to be detected, foreign particles that appear in the first measured result to the third measured result are judged as subjects on a position deeper than the second layer, and subjects that appear only in the first and the second measured results are judged as ones that exist in the first layer.

(9) The above-stated surface inspection method, wherein the body to be detected has a multilayer structure having a surface layer, a middle layer and a lower layer in order from surface, wherein subjects to be detected are mainly on the boundary of each layer, a first intensity of the optical flux having a long wavelength is set to a level higher than a disappearance level near a point where the detected signal from the internal subject disappears, a subject to be detected that belongs to the lower layer inside the body to be detected is measured based on the output of a first light intensity obtained by the optical flux having a long wavelength of the first intensity, a second intensity of the optical flux having a long wavelength is set to a level lower than the disappearance level, and a subject to be detected that belongs to the middle layer inside the body to be detected is measured based on the output from the first light intensity obtained by the optical flux having a long wavelength of the second intensity.

(10) The above-stated surface inspection method, wherein optical flux in the ultraviolet region is outputted as a short wavelength, while optical flux in the visible region is outputted as a long wavelength, and the body to be detected is a thin film SOI wafer, wherein layers of Si, $SiO_2$ and Si are formed as a multilayer structure in order from the surface of the thin film SOI wafer.

(11) The surface inspection method, wherein optical flux in the deep ultraviolet region (DUV: Deep Ultraviolet) is outputted as a short wavelength, the body to be detected is a wafer, and a subject to be detected on the wafer is foreign particles on the wafer surface and foreign objects including COPs or defects inside wafer.

(12) The surface inspection method, wherein optical flux having two types of wavelength, which are a short wavelength and a long wavelength, is outputted coaxially.

PREFERRED EMBODIMENTS OF THE INVENTION

The principle of a measurement method in a preferable example of the present invention will be described.

Figure 1:
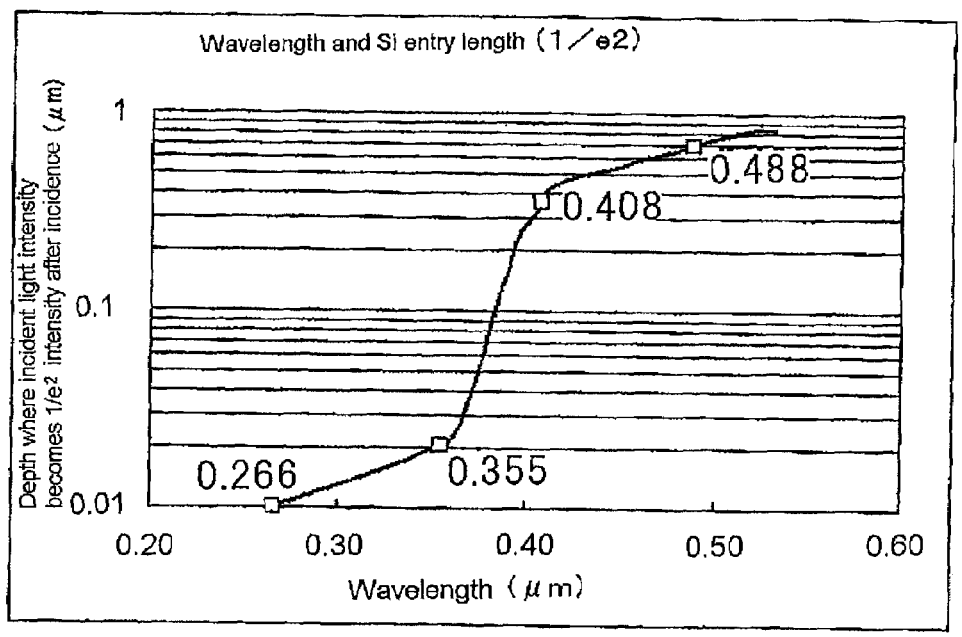
FIG. 1 is a graph showing relationship between wavelength and Si entry length (depth)

Relationship between depth and wavelength where incident light intensity becomes $1/e^2$ (approximately 13%) in Si by each wavelength is as shown in the graph of FIG. 1.

As it is clear from FIG. 1, in a region between wavelength of the ultraviolet region (particularly, deep ultraviolet region) and wavelength of the visible region, transmitting distance in Si drastically changes so as to be different by 10 times or more. Therefore, in the case of detecting by irradiating the light having a wavelength in the ultraviolet region, it only detects foreign particles or COP on approximate surface, whereas it is irradiated deep inside the wafer when light having a wavelength in the visible region is used. For this reason, detection of film constitution (multiple structure) inside the wafer, which is COP (COP having the largest number and most characteristic) on the boundary of a middle layer and a lower layer, for example, is made possible.

Figure 2:
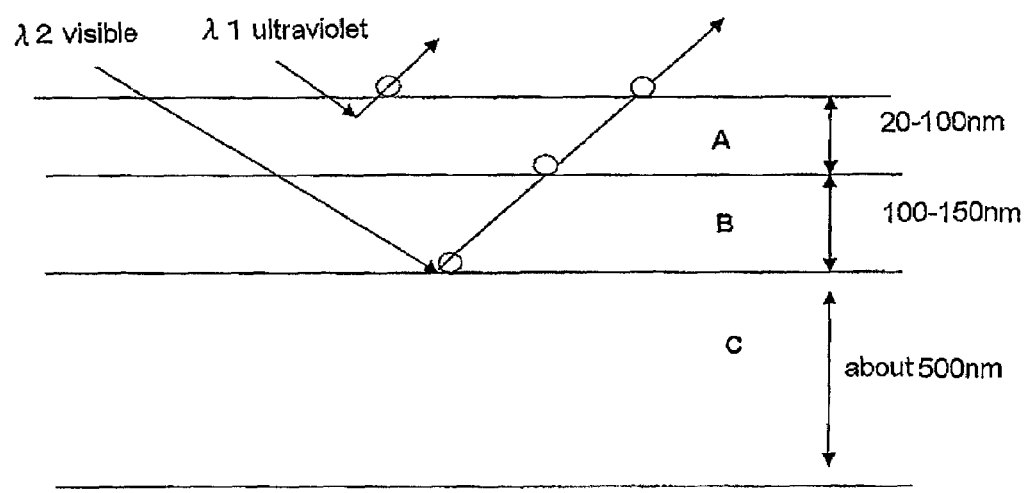
FIG. 2 is a view for explaining the measurement principle of the surface layer and the inside of a wafer in the surface inspection method of wafer by the present invention.

In FIG. 2, the wafer has a surface layer A made of Si (the first layer), a middle layer B made of $SiO_2$ (the second layer), and a lower layer C made of Si (the third layer). The thickness of the surface layer A is 20 to 100 nm. The thickness of the middle layer B is 100 to 150 nm, and the thickness of the lower layer C is approximately 500 nm.

The lower layer C in the example of FIG. 2 is also called as a base material

In a preferable example of the present invention, light $\lambda 1$ having the wavelength of ultraviolet ray (short wavelength) is irradiated first in performing measurement to obtain the first measured result. Next, light $\lambda 2$ having the wavelength of visible light of high intensity (long wavelength), which is capable of detecting the inside (e.g. COPs in the lower layer that is the third layer C), is irradiated to obtain a detected image. Intensity is lowered to a level where subjects other than the first measured result disappear, and the level at the disappearance point is used as a standard level. The standard level is increased upward by a predetermined level to make it the first measurement level. The second measured result is obtained by measuring at the first measurement level. Moreover, the third measured result is obtained by measuring at the second measurement level that is lowered downward by the standard level.

The subjects (foreign particles) are measured based on the measured result obtained in this manner. For example, a subject to be detected that appears only in the first measured result is judged as one that exists on wafer surface. Foreign particles that appear in the first to the third measured results are judged as subjects on a position deeper than the middle layer (the second layer). Subjects that appear only in the first and the second measured results are judged as ones that exist on the surface layer (the first layer).

By executing such measurement, even in the case of wafers having different multilayer structures (film conditions), measurement can be performed by irradiating light having upper and lower predetermined levels of the standard level (or level higher and level lower than the standard level), sizes of subjects inside a wafer, which exist in each layer or on each boundary, can be measured with reliability depending on the size of scattering light.

Note that COP is an acronym for Crystal Originated Particle, and it refers to fine particles on a wafer and crystal cavities inside a wafer.

Further, the SOI wafer refers to a Silicon on Insulator wafer.

An example of the surface inspection method based on the above-described measurement principle will be described, referring to FIGS. 3 to 6.

First, to measure the first layer 31a being the surface layer of a wafer 31 and the second layer 31b and the third layer 31c being the internal middle layer and lower layer, light having two types of wavelength are used. That is, laser beam 32 having a short wavelength (light having 355 nm or 266 nm) which is called a DUV (deep ultraviolet ray) and laser beam 33 that is visible light and has a long wavelength (light having 408 nm or 488 nm, for example) are used.

Figure 3:
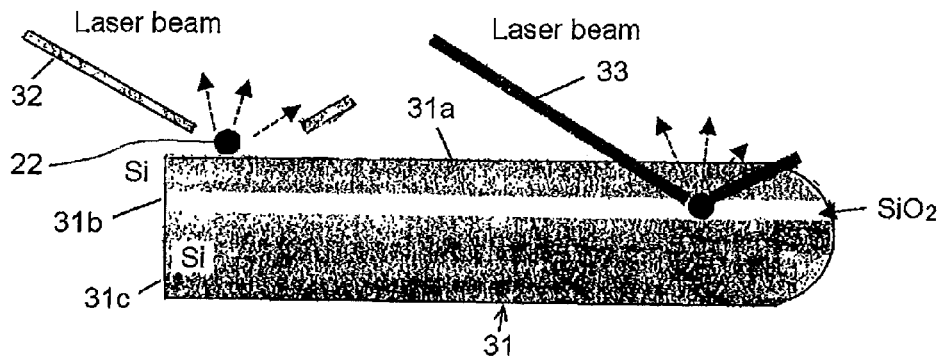
FIG. 3 is an explanatory view specifically showing the measurement of the surface layer and the inside of a wafer in the surface inspection method of wafer by the present invention.

As shown in FIG. 3, in the case where the first layer 31a is made of Si, the second layer 31b is made of $SiO_2$, and the third layer 31c is made of Si, it is possible to measure only the first layer 1a (surface layer) by the light having a short wavelength 32, because the light having a short wavelength 32 (DUV) usually does not transmit the first layer 31a made of Si. Although the light having a long wavelength 33 can measure the inside (the second layer 31b and the third layer 31c), depth, to which measurement can be performed, changes depending on the intensity of laser beam (optical flux).

First, the light having a short wavelength 32 is irradiated to obtain the first measured result, and then, the light having a long wavelength with high intensity 33 capable of detecting COP in the internal second layer 31b is irradiated to obtain a detected image. Intensity is lowered to a level where subjects other than the first measured result disappear, and it is used as the standard level. The second measured result is obtained by measuring at the first measurement level (upper measurement level) that is increased upward by a predetermined level from the standard level. Moreover, the third measured result is obtained by measuring at the second measurement level that is lowered downward by a predetermined level from the standard level. Then, a subject that appears only in the first measured result is considered as one that exists on the wafer surface. Foreign particles that appear in the first to the third measured results are judged as subjects on a position deeper than the second layer. A subject that appears only in the first and the second measured results are judged as subjects that exit in the first layer.

Foreign particles inside and on the surface layer of the wafer 31 can be identified and measured based on the measured result obtained by the above-described light having two types of wavelength. Particularly, foreign particles in each layer inside the wafer (i.e. the second layer and the third layer) and foreign particles in the surface layer can be identified and measured.

Figure 4:
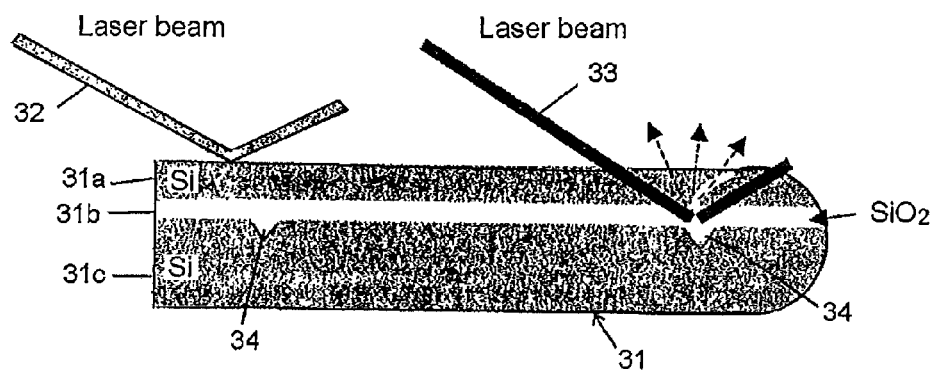
FIG. 4 is a view for explaining the calibration on the long wavelength side.

Preferably, as shown in FIG. 4, by using the wafer 31 having many characteristic COP 34 in the base material that is the third layer 31c (lower layer), calibration on the long wavelength side is made possible. For example, when the intensity of light quantity on the long wavelength side is adjusted to set the intensity to "Strong or High" first, for example, all layers of the wafer 31 are measured, and then, as the intensity is adjusted from "High" to "Weak or Low", the COPs 34 in the lower layer 31c disappear, and they cannot be measured. Generally, since many COPs intensively exist on the surface of the lower layer 31c (base material) of the wafer 31, in other words, boundary between the middle layer 31b and the lower layer 31c, a large number of characteristic COPs 34 that intensively exist on the surface of the lower layer 31c of the wafer 31 intensity level disappear by the above-described intensity adjustment from "Strong or High" to "Weak or Low". When this phenomenon is used, optimum light quantity for measuring the COPs 34 that exist in the base material of the wafer 31, i.e. the third layer 31c (lower layer) is formed, and calibration can be easily and accurately performed.

Figure 5:
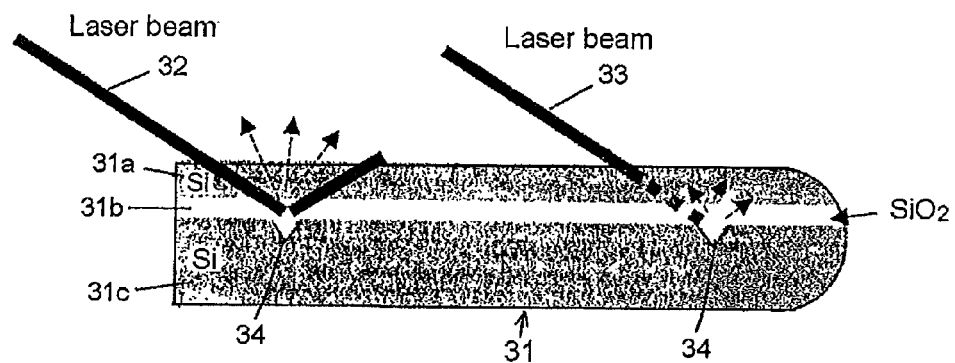
FIG. 5 is an explanatory view showing a state before/after the disappearance of internal COP by the adjustment of the intensity of a long wavelength.

Further, as shown in FIG. 5, foreign particles on the lower layer 31c can be judged on the basis of a difference of foreign particles detected before and after the COPs 34 on the wafer lower layer 31c disappear. That is, first, before the COPs 34 disappear, foreign particles are previously detected and recorded. Next, residual foreign particles are obtained, by subtracting foreign particles after the COPs 34 disappear, from foreign particles before the COPs 34 disappear. Such residual foreign particles can be judged as foreign particle on the lower layer 31c.

When such a phenomenon is utilized, calibration can be performed by using the COPs on the lower layer. For example, by performing measurement at least twice on different conditions, foreign particles that belong to the surface, the surface layer, and inside (middle layer, lower layer) of the wafer can be identified and can be accurately measured.

Further, surface scattering is considered to include scattering on each interface depending on wavelength. For this reason, when the above-described calibration is performed, HAZE measurement (specifically, surface scattering measurement) is further performed, and it is assumed that the condition inside the wafer (middle layer, lower layer) be HAZE-A, and the condition where the internal COPs disappeared be HAZE-C, one obtained by subtracting HAZE-C from HAZE-A can be judged as HAZE information on the surface of the lower layer 31C of the wafer 31.

Figure 6:
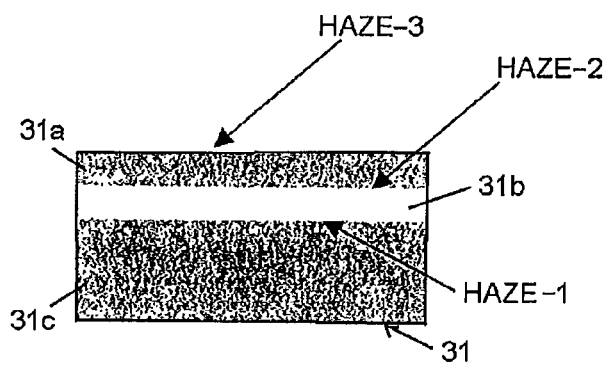
FIG. 6 shows HAZE from each interface.

For example, FIG. 6 shows HAZE of each interface of the upper layer 31a, the middle layer 31b and the lower layer 31c. Conditions where the COPs can be observed include HAZE-1, 2 and 3, and information of HAZE-2 and 3 is formed when the COP cannot be measured. Although coefficient by wavelength becomes necessary if a short wavelength is HAZE-3, HAZE information on each interface can be extracted by operation.

Figure 7:
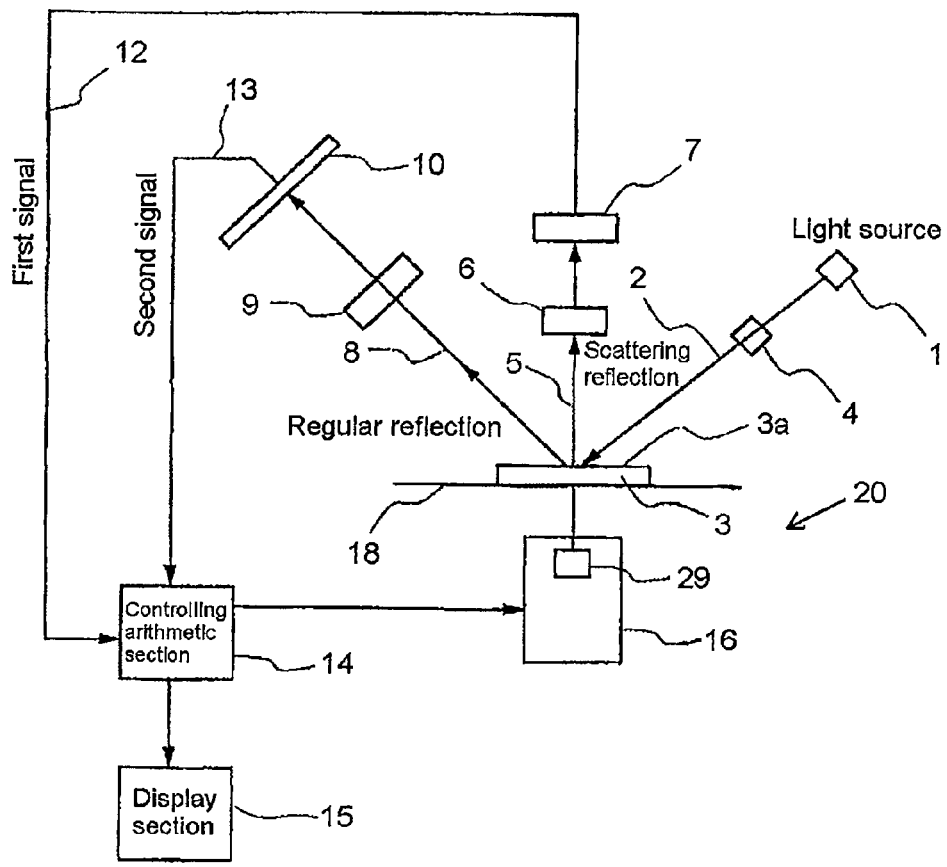
FIG. 7 is a schematic view showing an example of a surface inspection apparatus for implementing the present invention method.

FIG. 7 shows the surface inspection apparatus by one preferable example for implementing the present invention method.

In FIG. 7, the apparatus has: a light source section 1; an illumination optical system 4 that illuminates surface 3a to be detected of a wafer 3 (body to be detected) at a predetermined gradient angle by optical flux 2 of laser beam from the light source section 1; the first light-receiving optical system 6 that receives scattering reflection light 5 from the detected surface 3a; the first light intensity detecting section 7 that receives the scattering reflection light 5 received by the first light-receiving optical system 6; the second light-receiving optical system 9 that receives regular reflection light or specular reflection light 8 from the detected surface 3a; the second light intensity detecting section 10 that receives the regular reflection light or the specular reflection light 8 received by the second light-receiving optical system 9; and a controlling arithmetic section 14 that calculates the size of a foreign particle 22 on the surface to be detected 3a based on the first signal 12 from the first light intensity detecting section 7 or the height of foreign particle 22 on the surface to be detected 3a based on the second signal 13 from the second light intensity detecting section 10.

The light source section 1 outputs the optical flux having two types of wavelength, which are a short wavelength and a long wavelength, while the intensity is made variable.

The optical flux having two types of wavelength outputted from the light source section 1 is made incident to the detected surface of the body at a predetermined incident angle simultaneously or alternatively.

Based on a type of optical flux outputted from the light source section 1 and an output from the first light intensity detecting section 7, at least the intensity of optical flux having a long wavelength, which is outputted from the light source section 1, is adjusted by the controlling arithmetic section 14.

The controlling arithmetic section 14 compares an output from the first light intensity detecting section 7 in irradiating the optical flux having a short wavelength with an output from the first light intensity detecting section 7 in irradiating the optical flux having a long wavelength, identifies a signal that appears only in the output from the first light intensity detecting section 7 in irradiating the optical flux having a long wavelength as a detected signal from an internal subject, and adjusts the intensity of the optical flux having a long wavelength, calculates a disappearance level near a point where the detected signal from the internal subject disappears, sets the first intensity of the optical flux having a long wavelength to a level higher than the disappearance level, and measures the subject inside the body to be detected based on the output from the first light intensity detecting section 7 which is obtained by the optical flux having a long wavelength of the first intensity.

In the case where the body 3 to be detected has a multilayer structure comprising the surface layer, the middle layer and the lower layer in order from the surface, and the subjects to be detected are mainly on the boundary of each layer, the controlling arithmetic section 14 sets the first intensity of the optical flux having a long wavelength to a level higher than the disappearance level, measures a subject to be detected that belongs to the lower layer inside the body to be detected based on the output from the first light intensity detecting section 7 obtained by the optical flux having a long wavelength of the first intensity, sets the second intensity of the optical flux having a long wavelength to a level lower than the disappearance level, and measures a subject to be detected that belongs to the middle layer inside the body to be detected based on the output from the first light intensity detecting section 7 obtained by the optical flux having a long wavelength of the second intensity.

Further, the light source section 1 outputs the optical flux in the ultraviolet region as a short wavelength, and outputs the optical flux in the visible region as a long wavelength. Preferably, the light source section 1 outputs the optical flux in the deep ultraviolet region (DUV: Deep Ultraviolet) as a short wavelength. Further, the light source section 1 outputs the optical flux having two types of wavelength, which are a short wavelength and a long wavelength coaxially, while the intensity is made variable.

The controlling arithmetic section 14, in inspecting the wafer having the multilayer structure of the surface layer, the middle layer and lower layer (the first layer, the second layer and the third layer), irradiates light having a short wavelength to obtain the first measured result on one hand, irradiates light having a short wavelength of high intensity, which is capable of detecting COPs on the internal second layer, to obtain a detected image on the other hand, lowers intensity to a level where subjects other than the first measured result disappear to make it a standard level, performs measurement by the first measurement level higher than the level by a predetermined level to obtain the second measured result, furthermore, performs measurement by the second measurement level lower than the standard level by a predetermined level to obtain the third measured result, judges a subject that appears only in the first measured result as one that exists on the surface of the body to be detected, judges foreign particles that appear in the first to the third measured results as subjects on a position deeper than the second layer, judges subjects that appear only in the first and the second measured results as ones that exist in the first layer.

Further, in the case where the required size of foreign particle is approximately equal to or larger than the diameter of the optical flux 2 illuminated on the surface to be detected 3a, the controlling arithmetic section 14 can also calculate the height of the foreign particle 22 on the surface to be detected 3a based on the second signal 13.

In an embodiment of a height data HR method where the height of the foreign particle 22 is calculated from changes of height data (a so-called high resolution method where measurement is precisely performed at high density), the controlling arithmetic section 14 is constituted so as to judge the existence of the foreign particle 22 in the case where the first signal 12 from the first light intensity detecting section 7 is a predetermined slice level or more, and calculate the height of the foreign particle based on the second signal 13 in a region which is judged that the foreign particle 22 exists and the second signal 13 in a region around the region which is judged that the foreign particle 22 exists. The height of the foreign particle 22 is determined according to the average value of the second signal 13 in a predetermined region, and follows the waviness (including warp and other height changes) of the surface to be detected.

Further, the controlling arithmetic section 14 is constituted so as to calculate the height of the foreign particle 22 based on the difference of average values of data by the second signal 13 in a region which is judged that the foreign particle 22 exists and data by the second signal 13 in a region around the region which is judged that the foreign particle 22 exists.

Further, the above-described surface inspection apparatus can be also used in an embodiment employing a pixel method.

In such a case, the controlling arithmetic section 14 is constituted so as to partition the measurement subject 3 into a predetermined large number of pixels of unit region and treat the maximum value of the first signal 12 and/or the second signal 13 in each pixel as a value of each signal in the pixels.

In this case, the controlling arithmetic section 14 is constituted so as to calculate the height of the foreign particle 22 based on a difference of average values of data by the second signal 13 to which pixel process has been performed in the region which is judged that the foreign particle 22 exists and data by the second signal 13 to which pixel process has been performed in a region around the region which is judged that the foreign particle 22 exists.

Then, the controlling arithmetic section 14 is constituted so as to judge the existence of the foreign particle 22 based on the first signal 12 to which pixel process has been performed and calculate the height of the foreign particle based on each analog first signal 12 and analog second signal 13 in pixels at the position which is judged that the foreign particle 22 exists.

The controlling arithmetic section 14 includes a signal processing section, wherein a signal process result in the section (position, quantity, height, scattering reflection light level or the like of foreign particle) is displayed on a display section 15.

Further, the controlling arithmetic section 14 sends a control signal to a drive section 16, and controls the movement and the rotation of a table 18 mounting the wafer 3 in X-direction, Y-direction and Z (height)-direction.

Moreover, the controlling arithmetic section 14 also supplies a process signal to a robot arm drive section (not shown), which is used for operating the light source 1, the illumination optical system 4, the first light-receiving optical system 6, the first light intensity detecting section 7, the second light-receiving optical system 9, the second light intensity detecting section 10 and the wafer 3, to control it.

Regarding the surface inspection apparatus and method of the HR method and the pixel method for Z data (i.e. height data), technique explained in Japanese Patent Unexamined Publication No. 2000-337844 can be employed.

The controlling arithmetic section 14 outputs a control signal to the drive section 16 so as to perform predetermined control of a motor 29 and the light source 1, whereas it receives a signal containing rotation information by the drive section 16 (for example, pulse signal by a predetermined rotation of the motor 29 that rotates the wafer being the material to be detected) from an encoder section. The controlling arithmetic section 14 communicates data with the memory section if necessary and executes desired process.

A scanning section 20, which relatively displaces at least one of the optical flux 2 and the body to be detected 3 such that the optical flux 2 scans the surface to be detected 3a, is constituted by the drive section 16, the motor 29, the table 18 and the like.

According to the present invention, it is possible to manage the inside (middle layer, lower layer) of a thin film SOI that is called the next generation wafer and the interface between the layers. Conventionally, they have been managed by the electrical characteristics of a wafer and foreign particles on surface, but interface management can be performed according to the present invention better than conventional ones. For this reason, influence to yield can be minimized. The invention can remarkably contribute to yield improvement and quality improvement of materials.

The invention claimed is:

1. A surface inspection apparatus comprising:
a light source section that outputs an optical flux having two types of wavelength, which are a short wavelength and a long wavelength, while the intensity of the flux is made variable, wherein the light source section outputs the optical flux in the ultraviolet region as the short wavelength and outputs the optical flux in the visible region as the long wavelength;
an irradiation optical system that makes the optical flux having two types of wavelength outputted from said light source section, incident simultaneously or alternatively to a detected surface of a body to be detected, which is a subject of surface inspection at a predetermined incident angle;
a scanning section that relatively displaces at least one of said optical flux and said body to be detected in such a manner that said optical flux scans said detected surface;
a first scattering light detection optical system that guides scattering light outputted from the incident portion of said detected surface, to which said optical flux has been made incident, to a first light intensity detecting section;
a regular reflection light detection optical system that guides regular reflection light outputted from the incident portion of said detected surface, to which said optical flux has been made incident, to a second light intensity detecting section; and a controlling arithmetic section that adjusts at least the intensity of the optical flux having a long wavelength outputted from the light source section based on a wavelength of optical flux outputted from the light source section and an output from the first light intensity detecting section, wherein said controlling arithmetic section is constituted so as to compare the output from said first light intensity detecting section in irradiating the optical flux having a short wavelength, with the output from said first light intensity detecting section in irradiating the optical flux having a long wavelength, and then, identify a signal that appears only in the output from said first light intensity detecting section in irradiating the optical flux having a long wavelength, as a detected signal from an internal subject, and further adjusts the intensity of the optical flux having a long wavelength, and then calculates a disappearance level near a point where the detected signal from the internal subject disappears, further the controlling arithmetic section sets the first intensity of the optical flux having a long wavelength to a level higher than the disappearance level, and measures a subject inside the body to be detected based on the output from the first light intensity detecting section obtained by the optical flux having a long wavelength of the first intensity.

2. The surface inspection apparatus according to claim 1, wherein:
the body to be detected has a multilayer structure comprising a surface layer, a middle layer and a lower layer in order from surface, wherein subjects to be detected are mainly positioned on the boundary of each layer, and
the controlling arithmetic section is constituted so as to:
set the first intensity of the optical flux having a long wavelength to a level higher than the disappearance level;
measure a subject to be detected that belongs to the lower layer inside body to be detected based on the output from the first light intensity detecting section obtained by the optical flux having a long wavelength of the first intensity;
set the second intensity of the optical flux having a long wavelength to a level lower than the disappearance level; and
measure a subject to be detected that belongs to the middle layer inside the body to be detected based on the output from the first light intensity detecting section obtained by the optical flux having a long wavelength of the second intensity.

3. The surface inspection apparatus according to claim 2, wherein the body to be detected is a thin film SOI wafer, wherein layers of Si, SiO$_2$ and Si are formed as a multilayer structure in order from the surface of the thin film SOI wafer.

4. The surface inspection apparatus according to claim 2, wherein the light source section is constituted so as to output optical flux in the deep ultraviolet region (DUV: Deep Ultraviolet) as a short wavelength, and
wherein the body to be detected is a wafer, and a detected subject on the wafer is foreign particles on the wafer surface and foreign objects including COPs or defects inside the wafer.

5. The surface inspection apparatus according to claim 2, wherein the light source section is constituted so as to coaxially output the optical flux having two types of wavelength, which are a short wavelength and a long wavelength, and make the intensity of the flux variable.

6. The surface inspection apparatus according to claim 1, wherein the body to be detected is a thin film SOI wafer, wherein layers of Si, SiO$_2$ and Si are formed as a multilayer structure in order from the surface of the thin film SOI wafer.

7. The surface inspection apparatus according to claim 1, wherein the light source section is constituted so as to output optical flux in the deep ultraviolet region (DUV: Deep Ultraviolet) as a short wavelength, and
wherein the body to be detected is a wafer, and a detected subject on the wafer is foreign particles on the wafer surface and foreign objects including COPs or defects inside the wafer.

8. The surface inspection apparatus according to claim 1, wherein the light source section is constituted so as to coaxially output the optical flux having two types of wavelength, which are a short wavelength and a long wavelength, and make the intensity of the flux variable.

9. A surface inspection method in which an optical flux having two types of wavelength, which are a short wavelength in the ultraviolet region and a long wavelength in the visible region, is made incident to a detected surface of a body to be detected, which is a subject of surface inspection at a predetermined incident angle and foreign particles are detected, the method including the steps of:
adjusting the intensity of optical flux having a long wavelength so as to calculate a disappearance level near a point where a detected signal from an internal subject disappears,
setting a first intensity of the optical flux having a long wavelength to a level higher than the disappearance level, and
measuring a subject inside the body to be detected on the basis of the output of the first light intensity which is obtained by the optical flux having a long wavelength of the first intensity.

10. The surface inspection method according to claim 9, wherein a surface layer, a middle layer and a lower layer are a first layer, a second layer and a third layer, respectively,
a light having a short wavelength is irradiated to obtain a first measured result,
the light having a long wavelength of high intensity, which is capable of detecting foreign objects including COPs or defects on the third layer inside, is irradiated to obtain a detected image,
the intensity is lowered to a level where subjects other than the first measured result disappear to make it a standard level,
a second measured result is obtained by performing measurement by the first measurement level higher than the level by a predetermined level,
a third measured result is obtained by further performing measurement by the second measured level lower than the standard level by a predetermined level,
a subject that appears only in the first measured result is judged as one that exists on the surface of the body to be detected,
foreign particles that appear in the first measured result to the third measured result are judged as subjects on a position deeper than the second layer, and
subjects that appear only in the first and the second measured results are judged as ones that exist in the first layer.

11. The surface inspection method according to claim 9, wherein:
the body to be detected has a multilayer structure having a surface layer, a middle layer and a lower layer in order from surface, wherein subjects to be detected are mainly on the boundary of each layer, a first intensity of the optical flux having a long wavelength is set to a level higher than a disappearance level near a point where the detected signal from the internal subject disappears, a subject to be detected that belongs to the lower layer inside the body to be detected is measured based on the output of a first light intensity obtained by the optical flux having a long wavelength of the first intensity, a second intensity of the optical flux having a long wavelength is set to a level lower than the disappearance level, and a subject to be detected that belongs to the middle layer inside the body to be detected is measured based on the output from the first light intensity obtained by the optical flux having a long wavelength of the second intensity.

12. The surface inspection method according to claim 9, wherein the body to be detected is a thin film SOI wafer, wherein layers of Si, $SiO_2$ and Si are formed as a multilayer structure in order from the surface of the thin film SOI wafer.

13. The surface inspection method according to claim 9, wherein optical flux in the deep ultraviolet region (DUV: Deep Ultraviolet) is outputted as a short wavelength, the body to be detected is a wafer, and a subject to be detected on the wafer is foreign particles on the wafer surface and foreign objects including COPs or defects inside wafer.

14. The surface inspection method according to claim 9, wherein optical flux having two types of wavelength, which are a short wavelength and a long wavelength, is outputted coaxially.

* * * * *